United States Patent [19]

Linder

[11] Patent Number: 5,664,567
[45] Date of Patent: Sep. 9, 1997

[54] FENESTRATED NASOPHARYNGEAL AIRWAY FOR DRAINAGE

[76] Inventor: Gerald S. Linder, P.O. Box 1085, Pacific Palisades, Calif. 90272

[21] Appl. No.: 682,921

[22] Filed: Jul. 16, 1996

[51] Int. Cl.[6] .......................... A61M 15/08; A61M 25/00; A61M 29/00; A62B 7/00
[52] U.S. Cl. ................... 128/207.18; 128/911; 604/280; 606/199
[58] Field of Search ...................... 128/200.24, 200.26, 128/207.14, 207.18, 911, 912, DIG. 26; 604/93, 94, 175, 264, 280, 282, 327, 328, 355; 606/108, 199

[56] References Cited

U.S. PATENT DOCUMENTS

| | | | |
|---|---|---|---|
| 2,335,936 | 12/1943 | Hanlon . | |
| 3,260,258 | 7/1966 | Berman | 606/199 |
| 3,814,103 | 6/1974 | Fettel et al. | 128/207.18 |
| 3,867,946 | 2/1975 | Huddy | 128/207.18 |
| 3,872,515 | 3/1975 | Miner et al. | 2/168 |
| 3,885,561 | 5/1975 | Cami | 604/280 |
| 3,964,488 | 6/1976 | Ring et al. | 128/207.18 |
| 4,068,658 | 1/1978 | Berman . | |
| 4,280,500 | 7/1981 | Ono | 604/280 |
| 4,284,076 | 8/1981 | Hall | 128/207.18 |
| 4,300,550 | 11/1981 | Gandi et al. | 128/207.18 |
| 4,445,897 | 5/1984 | Ekbladh et al. | 604/280 |
| 4,449,974 | 5/1984 | Messingschlager | 604/280 |
| 4,465,481 | 8/1984 | Blake | 604/280 |
| 4,502,482 | 3/1985 | Deluccia et al. | 128/207.15 |
| 4,612,927 | 9/1986 | Krüger | 128/200.26 |
| 4,637,389 | 1/1987 | Heyden | 128/207.15 |
| 4,801,297 | 1/1989 | Mueller | 604/280 |
| 4,821,715 | 4/1989 | Downing | 128/207.18 |
| 4,852,565 | 8/1989 | Eisele | 128/207.14 |
| 5,024,220 | 6/1991 | Holmgreen et al. | 128/911 |
| 5,419,314 | 5/1995 | Christopher | 128/200.26 |
| 5,429,683 | 7/1995 | Le Mitouard | 128/206.24 |

FOREIGN PATENT DOCUMENTS

| | | | |
|---|---|---|---|
| 125238 | 4/1977 | Germany | 128/200.14 |
| 3002298 | 7/1981 | Germany | 604/280 |
| 3017065 | 11/1981 | Germany | 604/280 |
| 220978 | 6/1968 | Sweden | 606/199 |

OTHER PUBLICATIONS

"Oeuvres Complètes D'Ambroise Paré", J. F. Malgaigne, Tome Deunième, Paris, France, J. B. B Aillière, Royal Academy of Medicine Library, 1840.

*Primary Examiner*—Kimberly L. Asher
*Attorney, Agent, or Firm*—Cislo & Thomas

[57] ABSTRACT

A fenestrated nasopharyngeal airway providing fluid flow and pressure release from sinus ostia and the like. A fenestrated nasopharyngeal airway has lateral fenestrations along the central third of the nasopharyngeal tube. The fenestrations are generally two to three inches long and may be divided by separators into three sections to preserve stiffness and to hold open the fenestrations. Fluids produced by adjacent sinus ostia and the like may migrate into the lumen of the nasopharyngeal tube through the lateral fenestrations. Fluid collection is avoided, and fluid pressure arising from such fluid accumulation is relieved. Such fluids generally travel to the open distal end of the nasopharyngeal airway where it may be collected or otherwise disposed of by the body or health-care attendants. Additionally, probes and other diagnostic instruments may pass through the nasopharyngeal airway which protects the adjoining nasal mucosa. As fluid migration is allowed by the present invention, the fenestrated nasopharyngeal airway may be used on a long-term basis without threatening the patient's health.

7 Claims, 1 Drawing Sheet

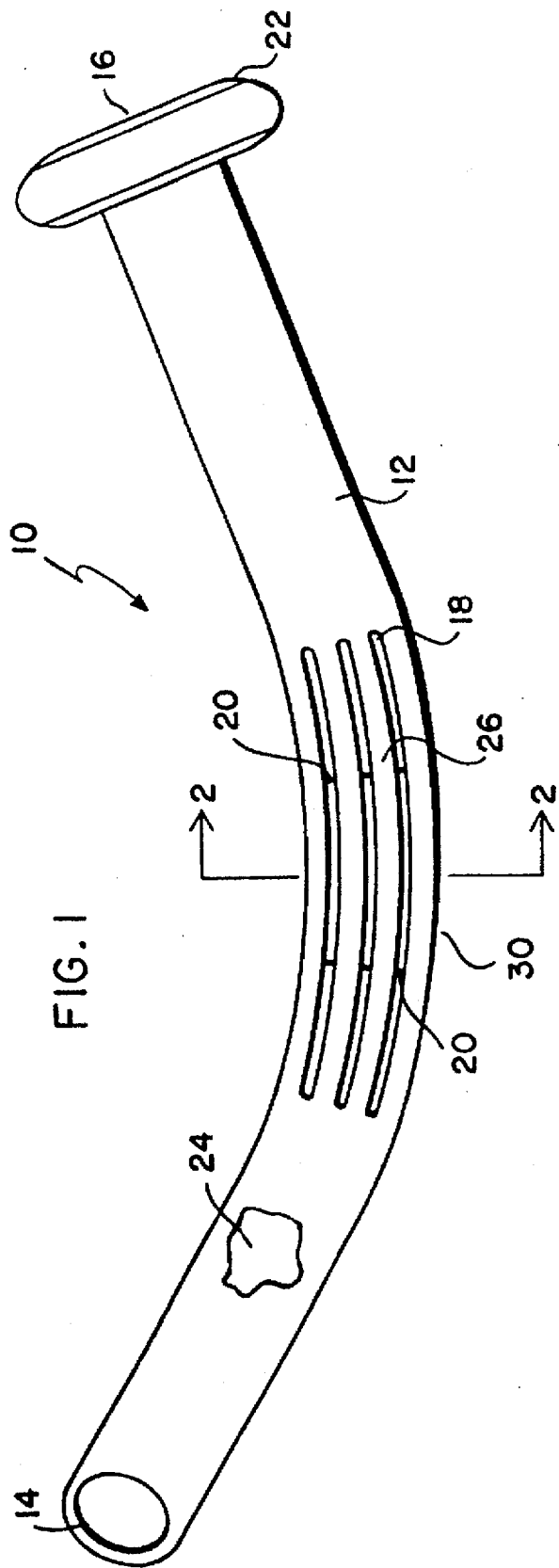
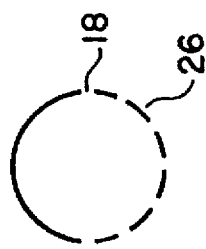

FENESTRATED NASOPHARYNGEAL AIRWAY FOR DRAINAGE

BACKGROUND OF THE INVENTION

1. Field of the Invention

The present invention relates to nasopharyngeal airways and more particularly to nasopharyngeal airways that allow drainage of fluids generated by the ostia of the various sinuses located in the skull and face.

2. Description of the Related Art

In the skull and face, various sinus ostia are located that generate fluids draining into the nasal cavity. These various sinuses include the frontal, maxillary, ethmoid, and sphenoid sinuses. As approximately a pint of sinus fluids are generated a day, the drainage of these fluids is an important aspect of good health. Should such fluids pool, collect, or otherwise be left undrained, sinus infections may occur. If the sinus ostia are not allowed drainage of their secretions, pressure may also build up causing headaches and other complications.

A nasopharyngeal airway (NPA) is generally a tubular device passing from the tip of one of the nares, or nostrils, to the oropharynx of the patient. Sterilized plastics and the like are considered common materials sufficiently flexible to accommodate the curved path the NPA must take in order to travel from the naris to the oropharynx. Generally, such NPAs are tubes with solid walls that do not allow any migration of sinus fluids (such as those generated by the sinus ostia) from the exterior of the NPA to its interior. While such NPAs have their uses, such uses are generally temporary in nature as longer term collection or blockage of the sinus fluids leads to the complications set forth above.

Below are several detailed descriptions of prior attempts in the art to achieve nasopharyngeal airways.

M. V. Downing, U.S. Pat. No. 4,821,715

This reference is directed to a nasopharyngeal airway. Referring to the figures, the patient 10 is provided with the nasopharyngeal airway 11 comprising a tube 12 which, when inserted through the nares 13, extends through the nasal passage 14 to the oropharynx 15 of the patient 10. The tube 12 has an inside wall 17 which defines an airway passage 18 (shown in FIG. 3). Several lumens 19 are formed within the inside wall 17 of the tube 12. The lumens 19 are operatively connected to an oxygen source 22. The airway described in the Downing patent includes no fenestrations.

R. F. Eisele, U.S. Pat. No. 4,852,565

This reference is directed to a fenestrated tracheostomy tube that provides a generally interference-free path through which a disposable inner cannula may be inserted. Referring to FIGS. 5 and 6, the improved fenestrated tracheostomy tube 40 has an outer cannula 42 that incorporates the fenestrations 44. The fenestrations 44 are positioned near the center of the arcuate length of the outer cannula, so as to be generally positioned in the center of the trachea of the patient, and can be described as two pairs of slotted fenestrations arranged in a chevron pattern. Both the tracheal insertion and chevron pattern depart from characteristics used in nasopharyngeal airways. In fact, the fenestrations in this device are used to allow the patient to breathe normally, allowing the patient to be weaned from the tracheostomy tube.

E. L. Heyden, U.S. Pat. No. 4,637,389

This reference relates to endotracheal and tracheostomy tubes and is directed to a tubular intubation device with an expansible channel for fluid collection. Referring to FIGS. 1, 5, and 9, a central fluid passage 24 provides respiratory gas exchange for the patient's lungs. An elongated channel 40 is integrally formed into the wall of passage 24 by way of innermost second wall portion 48 and is positioned to provide favorable access for secretions in a recumbent patient. Ports 42 present at spaced locations along the length of the passage 40 in the outer wall portion 46 allow fluid flow into the passage 40. Accumulated fluids may be removed by suction catheter 60. Active suctioning, not passive drainage, is required to remove the collected fluids. If the fluids are left uncollected, drainage may halt. No passive relief for pressure generated via the sinus ostia is disclosed.

J. T. Hanlon, U.S. Pat. No. 2,335,936

This reference is directed to a nasal dilating device for use only in the nares. The nasal dilating device 10 is made of an inert metal or plastic or other material not irritable to the mucous membrane. The device 10 having been inserted into the nasal passage of the patient permits air to be drawn inwardly through the openings 18 and the end opening 14 and into the lungs of the patient. The device does not extend to the oropharynx, does not allow intubation, and does not protect the delicate mucous membrane tissue of the sinuses. The inwardly deflecting wall sections 16 are alternated with strip-openings 17 to assist in the inward passage of air and also to permit untrammeled hair growth within the nasal passages. Thus, the end section 11 comprises alternating strip sections 16 and slotted opening sections 17 for air passage and not fluid drainage. The overall rigidity and configuration (overall shape) 18 prevents this device from operating as a nasopharyngeal airway and it is not meant for continuous use.

DeLuccia, deceased et al., U.S. Pat. No. 4,502,482

This reference is directed to an endotracheal tube complex (which is unlike a nasopharyngeal airway). Referring to FIGS. 1, 2 and 4, the end portion 22 is formed with a plurality of longitudinal slits 36 formed parallel to each other.

C. Krüger, U.S. Pat. No. 4,612,927

This reference is directed to an instrument for keeping clear the upper respiratory passages. Referring to the figures, note the plurality of slots 27 and 10 that are placed in parallel fashion along the laterally directed width of the device 1.

R. Gandi et al., U.S. Pat. No. 4,300,550

This reference is directed to a suction and oxygenation catheter. Referring to FIG. 1, the plastic tube 24 is inserted through the nasal passage 62 of the patient, and the tube 24 has at its furthermost end a plurality of openings 48, 50 for the passage of air therethrough. The distal positioning of these openings would not provide any advantages in an NPA.

K. Miner et al., U.S. Pat. No. 3,872,515

This reference is directed to rubber gloves. The surgical gloves are formed of a nonallergenic material such as silicone rubber.

A. Le Mitouard, U.S. Pat. No. 5,429,683

This reference is directed to a face mask for breathing. Referring to FIG. 2, the inside surface of the shell 1 of the mask receives a lining 6. The lining 6 is made of a flexible material such as a polyurethane foam covered in latex. However, if there are allergy problems, the skin of the lining may be provided with a silicone coating. Column 2, Lines 40–56.

In patients requiring long-term care, airway-management devices such as NPAs are sometimes required for the maintenance of a patent unobstructed airway. The same is sometimes similarly true for patients requiring emergency, acute, and/or chronic care. Without the ability of a nasopharyngeal airway to allow the release of pressure generated by the fluids secreted by the sinus and otic ostia, life-threatening infections can occur due to fluid accumulation. The eustachian tubes are particularly susceptible to such pressure and may suffer adversely should an infection establish itself. The increased pressure from such fluids cannot be relieved by nasal NPAs previously known in the art.

It would be to great advantage to provide a nasopharyngeal airway that provided means by which fluid pressure and accumulation could be respectively relieved and drained. Such an NPA may also function as a portal for introducing diagnostic probes and instruments for long term measurements of the patient.

SUMMARY OF THE INVENTION

The present invention dwells predominantly upon a fenestrated nasopharyngeal airway (NPA) that allows the drainage of accumulating fluids and relief from the pressure generated when such fluids are blocked. Such drainage and pressure relief are accomplished without compromising the structural integrity of the nasopharyngeal airway, an important consideration in light of the fact that not only may the patient be ventilated through the nasopharyngeal airway, but important diagnostic and sensing instruments may be introduced into the patient via the nasopharyngeal airway. Any structural compromise arising from the fenestrated nature of a nasopharyngeal airway might precipitate or allow patient injury during insertion of such instruments. Additionally, by maintaining the structural integrity of the nasopharyngeal airway, the fenestrations more easily maintain their ability to allow fluid migration as the nasopharyngeal airway structure surrounding the fenestrations supports and maintains the fenestrations in an open condition.

The fenestrated nasopharyngeal airway of the present invention comprises a nasopharyngeal tube of length approximately five to seven inches with a diameter of approximately half an inch. The distal end of the nasopharyngeal airway is open. The proximal end of the nasopharyngeal airway is also open and has about it a flange or other rim or ridge that serves to prevent further passage of the nasopharyngeal airway into the patient. The rim, or flange, also allows the contact of instruments with the flange instead of the patient so that any related injury or trauma to the patient from such contact is avoided.

The fenestrations of the nasopharyngeal airway of the present invention are generally one millimeter in width separated by a distance of approximately one millimeter. The fenestrations run longitudinally along the nasopharyngeal airway and may have supports or other separating structures holding the fenestrations open. The fenestrations are present on those aspects of the nasopharyngeal airway which assume a lateral reference to the patient's midline depending upon whether the insertion of the nasopharyngeal airway into the patient is through the right or left naris. The fenestrations encompass approximately half the circumference of the nasopharyngeal tube where it most closely engages the central portion of the nasal cavity and is in close proximity to the ostia of the various sinuses. Generally, this area of the nasopharyngeal airway carrying the fenestrations is approximately one third the total length of the nasopharyngeal airway at its central portion.

OBJECTS OF THE INVENTION

It is an object of the present invention to provide a means by which sinus fluid may be drained and any accompanying pressure released when a patient is intubated with a nasopharyngeal airway.

It is an object of the present invention to prevent infection, headaches, and other maladies arising from the use of a nasopharyngeal airway.

It is an object of the present invention to provide a nasopharyngeal airway that drains sinus ostia fluids and relieves an accompanying pressure that may arise from the blockage of such ostia.

It is an object of the present invention to provide a nasopharyngeal airway that provides fluid drainage and pressure release especially for patients requiring long term intubation of nasopharyngeal airway.

It is yet another object of the present invention to provide a fenestrated nasopharyngeal airway that allows for the introduction of probes or other diagnostic probes or instruments through the nasopharyngeal airway without inflicting trauma or injury to the patient.

It is another object of the present invention to provide a fenestrated nasopharyngeal airway that maintains structural integrity even though the walls of the nasopharyngeal tube are perforated by fenestrations.

These and other objects and advantages of the present invention will be apparent from a review of the following specification and accompanying drawings.

BRIEF DESCRIPTION OF THE DRAWINGS

FIG. 1 shows a plan view of the nasopharyngeal airway of the present invention.

FIG. 2 shows a cross section of the nasopharyngeal airway shown in FIG. 1 taken along line 2—2.

DESCRIPTION OF THE PREFERRED EMBODIMENTS

The present invention is directed towards a fenestrated nasopharyngeal airway (fenestrated NPA). The fenestrated NPA of the present invention provides means by which fluids that are secreted by the sinus ostia and the like in the skull and face of a patient may be drained and the accompanying pressure that might arise through lack of drainage relieved. By allowing drainage of the otherwise accumulating fluids, the fenestrated NPA prevents life-threatening infections arising from the accumulated fluids and headaches and other deleterious effects from the unrelieved pressure. The fenestrated NPA of the present invention also allows the introduction of diagnostic probes and instruments into the patient via the nasopharyngeal passage provided by the fenestrated NPA. The fenestrations of the fenestrated NPA do not detrimentally affect the structural integrity of the fenestrated NPA, providing protection for the sinus mucosa and the like from injury due to the introduction of such diagnostic instruments.

The fenestrated NPA of the present invention is generally tubular in shape having open proximal and distal ends with fenestrations running longitudinally along the central portion of the fenestrated NPA. The distal end of the fenestrated NPA is open to the interior of the tube, as is the proximal end. A rim, or flange, surrounds the proximal end of the fenestrated NPA.

As shown in FIG. 1, the fenestrated nasopharyngeal airway (fenestrated NPA) 10, has a nasopharyngeal tube 12 which extends approximately five to seven inches. The nasopharyngeal tube 12 has an open distal end 14 and an open proximal end 16. A series of lateral fenestrations 18 travel longitudinally along the midsection of the nasopharyngeal tube 10 and, as shown in FIG. 2, such lateral fenestrations 18 are distributed approximately halfway about the circumference of the nasopharyngeal tube 12. Separators 20 are occasionally present within the lateral fenestrations, providing support and separation of the opposite sides of the fenestrations. A rim, or flange, 22 circumferentially encircles the open proximal end 16 of the fenestration NPA 10

The nasopharyngeal tube 12 defines an interior lumen 24 which is surrounded by the nasopharyngeal tube 12. The nasopharyngeal tube 12 is generally made of hypoallergenic material such as PVC, polyurethane, or other medically approved materials which are flexible. As contemplated in the present invention, the fenestrated NPA 10 should not be constructed out of latex as latex generally has a greater propensity to elicit allergic or anaphylactic reactions in some patients. Such reactions are traumatic, interfere with the proper operation of the fenestrated NPA 10, and may injure or otherwise do harm to the patient.

The nasopharyngeal tube 12 is generally approximately three to seven inches long and one-quarter to three-quarters inch in diameter. The wall thickness of the nasopharyngeal tube 12 is on the order of one to two millimeters. An introducer or other device may be used to aid the introduction of the nasopharyngeal tube 12 of the fenestrated NPA 10 into the patient.

The lumen 24 provides clear and free passage from the open proximal end 16 to the open distal end 14 of the nasopharyngeal tube 12. The wall of the nasopharyngeal tube 12 protects the outlying sinus mucosa and other adjacent tissues from the trauma of instrument or probe insertion and ensures that an open passageway is achieved from the left or right naris at the open proximal end 16 to the oropharynx at the open distal end 14.

In the central third of a nasopharyngeal tube 12 are a series of several parallel slits or fenestrations 18. These parallel fenestrations 18 may be divided into three sections in order to maintain tube stiffness and nasopharyngeal tube 12 wall integrity. The lateral fenestrations 18 are separated into sections by means of separators 20 that may be made of the same material as the nasopharyngeal tube 12. The separators 20 also serve to hold the lateral fenestrations in an open condition to promote fluid migration into the lumen 24.

The lateral fenestrations 18 are generally one millimeter wide, and are separated from adjacent lateral fenestrations by a distance of one millimeter. The length, width, and separating distance between the lateral fenestrations are generally determined by the need for fluid drainage and fluid-pressure release. Generally, the dimensions regarding the lateral fenestrations 18, above, are believed to serve well these concerns.

Generally, nasopharyngeal airways are curved so that they may better fit the passageway through which the NPA must travel, and the same may be similarly true for the fenestrated NPA 10 of the present invention.

As shown in FIG. 2, the lateral fenestrations 18 are separated by strips 26 of nasopharyngeal tube 12 wall material. The lateral fenestrations 18 are generally located so that they are adjacent the sinus ostia or other fluid-producing tissue. Generally, this requires that the lateral fenestrations 18 assume a lateral reference with respect to the patient midline. This lateral relationship to the midline of the patient depends upon whether the insertion is through the left or right naris. Generally, the convex portion of the central third of the nasopharyngeal tube 12 is striated with the lateral fenestrations 18 divided by the separators 20. As the convex portion 30 of the nasopharyngeal tube 12 is generally proximate the fluid-generating tissues, the lateral fenestrations 18 are best placed there to provide drainage and release pressure.

About the open proximal end 16 of the nasopharyngeal tube 12 is a rim, or flange, 22 that serves to obstruct the further passage of the nasopharyngeal tube 12 into the patient. Due to the predetermined length of the nasopharyngeal tube 12, the engagement of the flange 22 with the opening of the adjacent naris serves to position the open distal end 14 at the oropharynx. The flange 22 may be constructed of the same materials as the nasopharyngeal tube 12 and may be approximately one inch in diameter centered upon the open proximal end 16. The flange 22 may be approximately one-quarter to one-third-inches thick and serves to protect the adjacent nares.

Having described the construction of the fenestrated nasopharyngeal airway 10 of the present invention, the fenestrated NPA 10 is put to use as follows and in accordance with generally known methods for intubating patients with nasopharyngeal airways. An introducer may be used and inserted into the lumen 24 of the nasopharyngeal tube 12 via the open proximal end 16. If the introducer may be so fashioned, it may be bent or shaped according to the anticipated patient's anatomy. Lubricating jelly or the like may be used to lubricate the exterior of the fenestrated NPA 10. In some recent introducers, a balloon or other inflatable device serves to temporarily seal the open distal end 14 and to provide a first curved surface that leads the way during intubation.

Caution should be taken to ensure that the convex portion 30 of the fenestrated NPA 10 is brought adjacent the fluid-producing tissue after intubation is complete. Once the fenestrated NPA 10 and introducer are ready, the distal end 14 of the fenestrated NPA is introduced into the left or right naris of the patient. Intubation then proceeds until the fenestrated NPA 10 is entirely intubated into the patient with the flange 22 resting against the open naris end. The introducer is then withdrawn, and the patient now maintains a patent and unobstructed airway from the nose to the oropharynx.

When fluids are secreted by the sinus ostia or the like, they may flow into the lumen 24 of the fenestrated NPA 10 and travel down to the open distal 14 end of the nasopharyngeal tube 12. No pressure buildup occurs and no fluids accumulate in the sinuses due to the migration of the fluids into the lumen 24 and subsequent flow therefrom. As a result of the fluid flow across the nasopharyngeal tube 12, the fenestrated NPA 10 of the present invention may be used continually and on a long-term basis without threat of injury to the patient. The risk of sinus infection due to fluid collection and/or the risk of headaches due to increased fluid pressure are reduced.

In alternative embodiments of the present invention, the lateral fenestrations may take other shapes or forms including round, oval, elliptical, rectangular, triangular, square and/or other geometrical shapes. However, it is contemplated that the parallel slit embodiment of the present invention produces generally less trauma to the nasal mucosa during insertion of the fenestrated NPA. 10. Additionally, diagnostic instruments, probes or the like may more easily pass through the lumen 24 of the fenestrated NPA 10 that has a parallel slit fenestration design.

While the present invention has been described with regards to particular embodiments, it is recognized that additional variations of the present invention may be devised without departing from the inventive concept.

What I claim is:

1. A fenestrated nasopharyngeal airway for passive drainage of secreted fluids, comprising:

a tube, said tube comprising hypoallergenic material and defining a lumen, said tube having an open proximal end separated by a predetermined length from an open distal end, said tube adapted to extend from the nares tip of a patient and terminating adjacent an oropharynx of the patient when said tube is completely inserted into the nasal passage of the patient, at least one portion of said tube being generally adjacent fluid-secreting tissue of the patient; and said tube defining a plurality of parallel slit fenestrations adjacent said tissue and allowing fluid secreted by said tissue to travel into said lumen, said fenestrations being present about approximately one half of the circumference of said tube and extending along a portion of said tube traversing a central portion of an adjacent nasal cavity, said parallel slits being one millimeter (1 mm) wide and being separated by at least one millimeter (1 mm), said parallel slits being parallel to a midline of the patient, said parallel slits being divided by separators maintaining said parallel slits in an open condition, said separators maintaining stiffness and wall integrity of the fenestrated nasopharyngeal airway; whereby pressure normally arising due to fluids secreted by the tissue of the patient is relieved by fluid travel into said lumen, preventing fluid collection, headaches, and infection;

the shape of said parallel slit fenestrations preventing trauma to the nasal mucosa of the patient when the fenestrated nasopharyngeal airway is inserted into the patient's nasal passage; and said hypoallergenic material preventing allergic reaction and anaphylaxis by said patient to the fenestrated nasopharyngeal airway.

2. A fenestrated nasopharyngeal airway for passive drainage of secreted fluids, comprising:

a tube, said tube defining a lumen having an open proximal end separated by a predetermined length from an open distal end, said tube, adapted to be inserted into the nasal passageway of a patient and to extend from the nares tip of the patient to at least adjacent the oropharynx of the patient when said tube is completely inserted into a nasal passage of the patient, at least one portion of said tube being adjacent a fluid-secreting ostium of the patient; and said tube defining a first normally open fenestration adjacent the ostium of the patient allowing fluids secreted by the ostium of the patient to travel into said lumen, there being a plurality of normally open fenestrations in side-by-side relationship wherein said fenestrations are of the same geometrical shape encircling approximately one half the circumference of said tube and extending along a portion of said tube traversing a central portion of an adjacent nasal cavity of the patient, said plurality of fenestrations comprising spaced parallel slits wherein said slits are about one millimeter (1 mm) wide and wherein said parallel slits are separated by at least one millimeter (1 mm) of the tube material and are divided by separators maintaining said parallel slits in an open condition, said separators maintaining stiffness and wall integrity of the fenestrated nasopharyngeal airway.

3. A method for draining fluids and relieving accompanying pressure in a patient intubated with a nasopharyngeal airway the steps comprising:

providing a nasopharyngeal airway having normally opened fenestrations and being of a size adapted to the inserted into the nasal passageway of the patient;

intubating the patient with the fenestrated nasopharyngeal airway; and allowing fluids to migrate into said fenestrated nasopharyngeal airway through said fenestrations in said fenestrated nasopharyngeal airway; wherein said tube comprises hypoallergenic material and defines a lumen, said tube having an open proximal end separated by predetermined length from an open distal end, said tube extending from the nares tip of a patient and terminating adjacent in oropharynx of a patient when said tube is completely inserted into a nasal passageway of a patient, at least one portion of said tube being generally adjacent fluid-secreting tissue of the patient and wherein said tube defines a plurality of parallel slit fenestrations adjacent the patient's tissue and allows fluids secreted by the patient's tissue to travel into said lumen, said fenestrations being present about approximately one half of the circumference of said tube and extending along a portion of said tube traversing a central portion of an adjacent nasal cavity, said parallel slits being about one millimeter (1 mm) wide and being separated by at least one millimeter (1 mm) of material of said tube, said parallel slits being parallel to a midline of the patient and being divided by separators maintaining said parallel slits in an open condition, said separators maintaining stiffness and wall integrity of the fenestrated nasopharyngeal airway, the shape of said parallel slit fenestrations preventing trauma to the nasal mucosa of the patient when the fenestrated nasopharyngeal airway is inserted into the patient's nasal passage and said tube further being of hypoallergenic material thereby preventing allergic reaction and anaphylaxis of the patient to the fenestrated nasopharyngeal airway, whereby pressure normally arising due to fluids secreted by the patient's tissue is headaches and infections relieved by the fluid travelling into said lumen thereby preventing fluid collection.

4. A fenestrated nasopharyngeal airway for passive drainage of secreted fluids, comprising:

a tube, said tube defining a lumen and having an open proximal end separated by a predetermined length from an open distal end, said tube adapted to be inserted into the nasal passageway of a patient and to extend from a nares tip of the patient and terminating adjacent an oropharynx of the patient when said tube is completely inserted into a nasal passage of the patient, at least one portion of said tube being adjacent a fluid-secreting ostium of the patient; and said tube defining normally open fenestrations adjacent the ostium, said normally open fenestrations allowing fluid secreted by the ostium of the patient to travel into said lumen, said fenestrations being parallel slits and being one millimeter (1 mm) wide and being present about approximately one half the circumference of said robe and extending along a portion of said tube traversing a central portion of an adjacent nasal cavity;

said parallel slits further being defined as separated by at least one millimeter (1 mm) and being divided by separators maintaining said parallel slits in an open condition, said separators maintaining stiffness and wall integrity of the fenestrated nasopharyngeal airway; whereby pressure normally arising due to said fluids secreted by the ostium of the patient being relieved by fluid travel into said lumen, thereby preventing fluid collection, headaches, and infection, and trauma to the nasal mucosa of the patient when the fenestrated nasopharyngeal airway is inserted into said nasal passage.

5. A fenestrated nasopharyngeal airway for passive drainage of secreted fluids, comprising:

a tube, said tube defining a lumen and having an open proximal end separated by a predetermined length from an open distal end, said tube adapted to be inserted into the nasal passageway of a patient and to extend from a nares tip of the patient and terminating adjacent an oropharynx of the patient when said tube is completely inserted into a nasal passage of the patient, at least one portion of said tube being adjacent a fluid-secreting ostium of the patient; and said tube defining normally open fenestrations adjacent the ostium, said normally open fenestrations allowing fluid secreted by the ostium of the patient to travel into said lumen, said fenestrations being parallel slits which are parallel to a midline of the patient and being one millimeter (1 mm) wide and being present about approximately one half the circumference of said tube and extending along a portion of said tube traversing a central portion of an adjacent nasal cavity;

said parallel slits further being defined as separated by at least one millimeter (1 mm) and being divided by separators maintaining said parallel slits in an open condition, said separators maintaining stiffness and wall integrity of the fenestrated nasopharyngeal airway; whereby pressure normally arising due to said fluids secreted by the ostium of the patient being relieved by fluid travel into said lumen, thereby preventing fluid collection, headaches, and infection, and trauma to the nasal mucosa of the patient when the fenestrated nasopharyngeal airway is inserted into said nasal passage.

6. A fenestrated nasopharyngeal airway for passive drainage of secreted fluids, comprising:

a tube, said tube comprises hypoallergenic material and defining a lumen and having an open proximal end separated by a predetermined length from an open distal end, said tube adapted to be inserted into the nasal passageway of a patient and to extend from a nares tip of the patient and terminating adjacent an oropharynx of the patient when said tube is completely inserted into a nasal passage of the patient, at least one portion of said tube being adjacent a fluid-secreting ostium of the patient; and said tube defining normally open fenestrations adjacent the ostium, said normally open fenestrations allowing fluid secreted by the ostium of the patient to travel into said lumen, said fenestrations being parallel slits and being one millimeter (1 mm) wide and being present about approximately one half the circumference of said tube and extending along a portion of said tube traversing a central portion of an adjacent nasal cavity;

said parallel slits further being defined as separated by at least one millimeter (1 mm) and being divided by separators maintaining said parallel slits in an open condition, said separators maintaining stiffness and wall integrity of the fenestrated nasopharyngeal airway; whereby pressure normally arising due to said fluids secreted by the ostium of the patient being relieved by fluid travel into said lumen, thereby preventing fluid collection, headaches, and infection, and trauma to the nasal mucosa of the patient when the fenestrated nasopharyngeal airway is inserted into said nasal passage and allergic reaction and anaphylaxis to the fenestrated nasopharyngeal airway by the patient is prevented.

7. A method for draining fluids and relieving accompanying pressure in a patient intubated with a nasopharyngeal airway, the steps comprising:

a. providing a nasopharyngeal airway having normally open fenestrations and of a size adapted to be inserted into the nasal passageway of the patient; and said nasopharyngeal airway further comprising:

a tube, said tube comprising hypoallergenic material and defining a lumen said tube having an open proximal end separated by a predetermined length from an open distal end, said tube extending from the nares tip and terminating adjacent an oropharynx of the patient when said tube is completely inserted into a nasal passage of the patient, at least one portion of said tube being generally adjacent fluid-secreting tissue of the patient; and said tube defining a plurality of parallel slit fenestrations adjacent the patient's tissue and allowing fluid secreted by the patient's tissue to travel into said lumen, said fenestrations being present about approximately one half of the circumference of said tube and extending along a portion of said tube traversing a central portion of an adjacent nasal cavity, said parallel slits being one millimeter (1 mm) wide and being separated by at least one millimeter (1 mm), said parallel slits being parallel to a midline of the patient, said parallel slits being divided by separators maintaining said parallel slits in an open condition, said separators maintaining stiffness and wall integrity of the fenestrated nasopharyngeal airway; whereby pressure normally arising due to fluids secreted by the patient's tissue is relieved by fluid travel into said lumen, preventing fluid collection, headaches, and infection;

the shape of said parallel slit fenestrations preventing trauma to the nasal mucosa of the patient when the fenestrated nasopharyngeal airway is inserted into the patient's nasal passage; and said hypoallergenic material preventing allergic reaction and anaphylaxis by the patient to the fenestrated nasopharyngeal airway;

b. intubating the patient with the fenestrated nasopharyngeal airway; and allowing the fluids to migrate into said fenestrated nasopharyngeal airway through the fenestrations present in said fenestrated nasopharyngeal airway.

* * * * *